(12) United States Patent
Kim (10) Patent No.: US 8,697,368 B2
(45) Date of Patent: Apr. 15, 2014

(54) DIAGNOSTIC MARKER FOR LUNG CANCER COMPRISING HPαR AS ACTIVE INGREDIENT

(75) Inventor: Il Han Kim, Daejeon (KR)

(73) Assignee: Paichai University-Academic Cooperation Foundation, Daejeon (KR)

( * ) Notice: Subject to any disclaimer, the term of this patent is extended or adjusted under 35 U.S.C. 154(b) by 0 days.

(21) Appl. No.: 13/514,668

(22) PCT Filed: Jun. 29, 2011

(86) PCT No.: PCT/KR2011/004730
§ 371 (c)(1),
(2), (4) Date: Jun. 8, 2012

(87) PCT Pub. No.: WO2013/002434
PCT Pub. Date: Jan. 3, 2013

(65) Prior Publication Data
US 2013/0157291 A1    Jun. 20, 2013

(51) Int. Cl.
*G01N 33/53*    (2006.01)
*G01N 33/00*    (2006.01)
*G01N 33/574*   (2006.01)

(52) U.S. Cl.
USPC ......... 435/7.1; 435/7.92; 435/7.93; 435/7.94; 435/7.95; 435/7.23

(58) Field of Classification Search
None
See application file for complete search history.

(56) References Cited

U.S. PATENT DOCUMENTS

| | | | |
|---|---|---|---|
| 7,112,408 | B2 | 9/2006 | Ye et al. |
| 2008/0160546 | A1 | 7/2008 | Colpitts et al. |
| 2010/0179067 | A1 | 7/2010 | Patz, Jr. et al. |
| 2010/0248290 | A1 | 9/2010 | Lam et al. |

OTHER PUBLICATIONS

Mikkat et al., Proteomics, 2004, 4: 3921-3932.*
Bharti, et al., "Haptoglobin alpha-Subunit and Hepatocyte Growth Factor can Potentially Serve as Serum Tumor Biomarkers in Small Cell Lung Cancer," Anticancer Research, vol. 24, pp. 1031-1038, 2004.
Hoagland IV, et al. "Haptoglobin and Posttranslational Glycan-Modified Derivatives as Serum Biomarkers for the Diagnosis of nonsmall Cell Lung Cancer," American Cancer Soceity, vol. 110, No. 10, pp. 2260-2268, Nov. 17, 2007.
PCT International Search Report dated Mar. 20, 2012, issued in connection with the corresponding PCT Application No. PCT/KR2011/004730 (4 pages).

* cited by examiner

*Primary Examiner* — Hong Sang
(74) *Attorney, Agent, or Firm* — Lucas & Mercanti, LLP (57) ABSTRACT

Disclosed is a diagnostic marker for lung cancer comprising HpαR as an active ingredient. Because blood, which is relatively easy to sample, is employed as a specimen, the diagnostic kit and marker for lung cancer is very simple and does not subject patients to a load compared to conventional methods that are directed to a biopsy. In addition, the kit and marker of the present invention is useful in the early diagnosis of lung cancer thanks to its high diagnostic sensitivity and selectivity.

7 Claims, 6 Drawing Sheets

DIAGNOSTIC MARKER FOR LUNG CANCER COMPRISING HPαR AS ACTIVE INGREDIENT

CROSS-REFERENCE TO RELATED APPLICATIONS

This application is a 371 of PCT/KR2011/004730, filed Jun. 29, 2011, the entire contents of each of which are incorporated herein by reference.

TECHNICAL FIELD

The present invention relates to a diagnostic marker for lung cancer, comprising HPαR as an active ingredient and a method for the diagnosis of lung cancer, using the same.

BACKGROUND ART

With the increase in the smoking population and the aggravation of air pollution, lung cancer cases have rapidly increased in South Korea. A Korean statistical report has it that lung cancer cases rank first after stomach cancer in men and come next after breast cancer, uterine cancer, stomach cancer and colorectal cancer in women, and is associated with the highest rate of mortality in both men and women.

The frequency of incidence of lung cancer and the mortality rate from lung cancer in Korea are expected to increase for a significant period of time in the future in light of the current trend of an increasing smoking rate. As cancerous cells grow, the lung cancer causes various symptoms including vascular invasion into adjacent tissues, airway blockage, metastasis to lymph nodes, etc. Approximately 10-15% of lung cancer cases absent of any symptoms are diagnosed during a regular checkup. In most cases, lung cancer, when diagnosed, has already progressed to stage III or beyond, so that they are, for the most part, difficult to cure. Therefore, the early diagnosis of lung cancer is presenting itself as an urgent problem to be solved so that the mortality from lung cancer can be reduced.

Various methods are used in combination to diagnose lung cancer. So far, a number of lung cancer screening tests have been employed, including examination of tumor size, metastasis to lymph nodes, immunohistochemistry of biopsy samples of tumerified lung tissue or lymph nodes, chest X-ray screening, chest computerized tomography, and bronchoscopy. Lung cancer shows up in chest computerized tomography only if the size of the tumor is 0.1 cm or larger. However, lung cancer by this time has probably already metastasized to other tissues. In bronchoscopy, the inside of the lung can be directly observed with an endoscope, but there is the problem of spatial limitation that makes it difficult to observe tumors in deep places.

To supplement such lung cancer screening methods, attempts have been made to use the levels of CBC (complete blood count), serum electrolytes (including calcium), alkaline phosphatase, albumin, AST (aspartate aminotransferase), ALT (alanine transaminase), total bilirubin or creatinine, to diagnose lung cancer. Although studied for their values as diagnosis or prognosis factors, the application of conventional tumor markers is accompanied by limitations, and there are no officially recommended lung cancer markers.

Haptoglobin (Hp) is a protein that is redundantly found in the blood, like albumin. The serum protein is synthesized mainly in hepatocytes, dermal cells, pulmonary cells and renal cells and released into the blood. It exists as a tetrameric protein consisting of two α- and two β-chains, connected by disulfide bridges. In blood plasma, haptoglobin binds free hemoglobin released from erythrocytes and thereby inhibits its oxidative activity (Wassell J.(2002) Haptoglobin: function and polymorphism. Clin Lab. 46, 547-552/Langlois M. R. & Delanghe J. R. (1996) Biological and clinical significance of haptoglobin polymorphism in humans. Clinical Chemistry 42, 1589-1600). A recent research report on proteomic research showed that haptoglobin, although in a very small amount, is released from subcutaneous and abdominal adipocytes. The protein is synthesized in the adult liver, but not in the fetal liver. Haptoglobin is an acute phase protein (APP), whose plasma level rapidly increases in response to any infection or inflammatory process.

Haptoglobin exists in two allelic forms in the human population, so-called Hp1 and Hp2, the latter having arisen due to the partial duplication of Hp1 gene. Three genotypes of Hp, therefore, are found in humans: Hp1-1, Hp2-1, and Hp2-2 (Maeda N, McEvoy S M, Harris H F, Huisman T H, Smithies O. (1986) Polymorphisms in the human haptoglobin gene cluster: chromosomes with multiple haptoglobin-related (Hpr) genes. Proc Natl Acad Sci USA. 83, 73957399/Patzelt D, Geserick G, Schroder H. (1988) The genetic haptoglobin polymorphism: relevance of paternity assessment. Electrophoresis 9, 393397). There are two Hp alpha chain (Hpα) isoforms: alpha 1 and alpha 2. These alpha proteins exist as position variants in various species (Sadrzadeh S M, Bozorgmehr J. (2004) Haptoglobin phenotypes in health and disorders. Am J Clin Pathol. 121 Suppl: S97-104).

Among the diseases associated with the gene for the protein are diabetic nephropathy and Crohn's disease. As haptoglobin is indeed an acute-phase protein, any inflammatory process such as infection, extreme stress, burns, major crush injury, allergy, etc. may increase the levels of haptoglobin in the plasma. A recent report demonstrates that patients with cancer including ovarian cancer have elevated levels of plasma haptoglobin.

However, much study must be done to examine whether heptoglobin can act as a diagnostic marker for lung cancer. Accordingly, there is a need for a marker by which lung cancer can be specifically diagnosed and prognosticated.

DISCLOSURE

Technical Problem

Culminating in the present invention, inventive and thorough research into the early diagnosis and accurate prognosis of lung cancer led to the finding that patients with lung cancer have significantly increased serum HpαR levels.

Technical Solution

It is therefore an object of the present invention to provide a diagnostic marker for lung cancer, comprising HpαR as an active ingredient.

It is another object of the present invention to provide a diagnostic kit for lung cancer, comprising an antibody specifically binding to HpαR.

It is a further object of the present invention to provide a method for diagnosing lung cancer, comprising measuring the concentration of HpαR in blood. In one embodiment, the blood is a serum sample.

Advantageous Effects

Because blood, which is relatively easy to sample, is employed as a specimen, the diagnostic kit for lung cancer in accordance with the present invention is very simple and does not subject patients to a load compared to conventional methods that are directed to a biopsy. In addition, the kit of the present invention is useful in the early diagnosis of lung cancer thanks to its high diagnostic sensitivity and selectivity.

BEST MODE

Unless stated otherwise, all technical and scientific terms used in the specification, examples and appended claims have the meanings defined below.

The term "HpαR," as used herein, refers to a position variant of haptoglobin alpha 2 chain which undergoes a position change on 2D gel due to the C-terminal arginine residue (R).

The term "HpαQ," as used herein, refers to a position variant of haptoglobin alpha 1 or 2 chain which lacks the C-terminal arginine residue of haptoglobin alpha 1 or 2 chain.

The term "VR antibody," as used herein, refers to an antibody constructed to detect only the C-terminal arginine-containing moiety of HpαR, a haptoglobin variant which is particularly sensitive to lung cancer.

The term "VQ antibody," as used herein, refers to an antibody constructed to detect only the C-terminal glutamine (Gln, Q)-containing moiety of HpαQ.

Below, a detailed description will be given of the present invention.

In the present invention, when serum proteins from normal controls and lung cancer patients were spread on gel by 2D electrophoresis, an increase in the protein spot was only found in the patient group. MALDI-TOF analysis identified this lung cancer marker candidate as a haptoglobin alpha chain variant which undergoes a position change on 2D gel due to the C-terminal arginine.

Based on the 2D electrophoresis result indicating the association of HpαR with lung cancer, an immunochemical assay on blood samples of lung cancer patients using an antibody which was adapted to specifically bind to HpαR yielded a significant data demonstrating that HpαR could be useful as a diagnostic marker for lung cancer.

Hence, in accordance with an aspect thereof, the present invention provides a diagnostic marker for lung cancer, comprising HpαR as an active ingredient.

In an embodiment of the present invention, blood samples from normal controls and lung cancer patients were monitored for HpαR level using ELISA. As a result, the blood HpαR level was found to increase with the progress of lung cancer. In contrast, blood HpαQ levels were observed to increase as lung cancer developed into stage II, but decrease as lung cancer further developed into stage III/IV. As for Hpα and Hpβ, their levels in the blood were increased at the onset of lung cancer, but significantly decreased with the progress of lung cancer. Therefore, because only the blood HpαR level increases with an increase in the stage of lung cancer, HpαR is identified as a marker that can trace the progress of lung cancer.

In accordance with another aspect thereof, the present invention provides a diagnostic kit for lung cancer, comprising an antibody specifically binding to HpαR.

The diagnostic kit of the present invention may comprise a device and a reagent which are generally used in immunological analysis in the art, in addition to the antibody specifically binding to HpαR, and may be readily prepared in a typical manner.

According to one embodiment of the present invention, the diagnostic kit for lung cancer may comprise an antibody specifically binding to HpαR; a secondary antibody conjugate with a label that can react with a substrate to cause a chromatic change; a substrate solution which develops a color upon reaction with the label; a washing buffer and a reaction stop buffer.

To diagnose lung cancer, the diagnostic kit in accordance with the present invention is operated in such a manner that the antigen is qualitatively and quantitatively analyzed by means of an antigen-antibody reaction. The antigen-antibody reaction may be assayed using a typical method, such as ELISA, radioimmunoassay (RIA), sandwich assay, Western blotting, immunoprecipitation immunohistochemical staining, fluorescent immunoassay, enzyme-substrate coloring assay, and antigen-antibody aggregation. For example, a diagnostic kit may comprise 96-well microtiter plates the wells of which are coated with a specimen or a control so as to allow the ELISA assay to be performed with recombinant monoclonal antibodies.

Examples of the immobilizer on which an antigen-antibody reaction occurs include a nitrocellulose membrane, a PVDF (polyvinylidene difluoride) membrane, a well plate formed of polyvinyl resin or polystyrene resin, a slide glass, and a resin for protein binding.

The label conjugated to the secondary antibody is preferably a coloring agent which can bring about a color change as it reacts with its substrate. Representative among them are HRP (horseradish peroxidase), alkaline phosphatase, colloid gold, fluorescein such as FITC (poly L-lysine-fluorescein isothiocyanate) and RITC (rhodamine-B-isothiocyanate), and dye.

As for the substrate solution, it is dependent on the label. Examples include TMB (3,3',5,5'-tetramethyl bezidine), ABTS [2,2'-azino-bis(3-ethylbenzothiazoline-6-sulfonic acid)], and OPD (o-phenylenediamine). The coloring substrate is preferably provided in the form of a solution in buffer (0.1M The washing solution preferably contains phosphate buffer, NaCl and Tween® 20. More preferable is a solution (PBST) containing 0.02M phosphate buffer, 0.13M NaCl, and 0.05% Tween® 20. After the antibody is allowed to react with the antigen, the antigen-antibody complex is treated with the secondary antibody conjugate, followed by immobilization and then washing 3-6 times with the washing solution. A sulfuric acid solution may be used to stop the enzymatic reaction.

In accordance with a further aspect thereof, the present invention provides a method for diagnosing lung cancer, comprising measuring the concentration of HpαR in blood. In this context, lung cancer may be diagnosed or predicted by detecting the lung cancer marker HpαR by means of an antigen-antibody reaction using an antibody specifically binding to HpαR.

A better understanding of the present invention may be obtained from the following examples which are set forth to illustrate, but are not to be construed as limiting, the present invention.

EXAMPLES

Example 1

Subjects

All sera of normal persons (control) and lung cancer patients were obtained from white Caucasians. To make them suitable for a biomarker study, all the sera were collected and treated according to the instructions of the FDA (Food and Drug Administration) and the NCI (National Cancer Institute). They were prepared from the blood collected after the approval of the IRB and the HIPAA. All the sera and the clinical information thereof were provided from Bioserve (U.S.A.) as summarized in Table 1, below.

TABLE 1

| Characteristics | No. of samples |
| --- | --- |
| Non-small Cell Lung Cancer (NSCLC) | 60 |
| Male | 60 |
| Mean age (years) | 57.16 ± 17.33 (26-91) |
| Cancer Stage | |
| Stage I | 20 |
| Stage II | 20 |
| Stage III | 14 |
| Stage IV | 6 |
| Sub-type | |
| Adenocarcinoma | 28 |
| Papillary Adenocarcinoma | 2 |
| Adenosquamous cell carcinoma | 2 |
| Squamous Cell Carcinoma | 20 |
| Acinar cell carcinoma | 3 |
| N/A | 5 |
| Cancer Grade | |
| poorly differenciated | 22 |
| Moderately differenciated | 22 |
| Well differenciated | 1 |
| N/A | 15 |

ELISA (Enzyme-linked immunosorbent assay) was performed to quantitatively analyze blood proteins.

Sera obtained after the centrifugation of blood samples taken from normal persons and lung cancer patients were used for quantitative protein analysis with an ELISA kit using antibodies of interest (Express® ELISA kit (rabbit), GenScript). In this regard, mono-specific antibodies to respective antigens were obtained by injecting purified peptide-KLH conjugates into rabbits to form antisera and purifying the antisera on a peptide-affinity column to which the peptide was bound.

A standard curve was made from the absorbance at 450 nm of various concentrations of each antigen peptide. Serum protein levels were determined with reference to the standard curve from mean values of three measurements of absorbance at 450 nm. For statistical analysis, the software GraphPad Prism® (ver. 5.04) (GraphPad Software) was used.

Example 2

Figure 1:
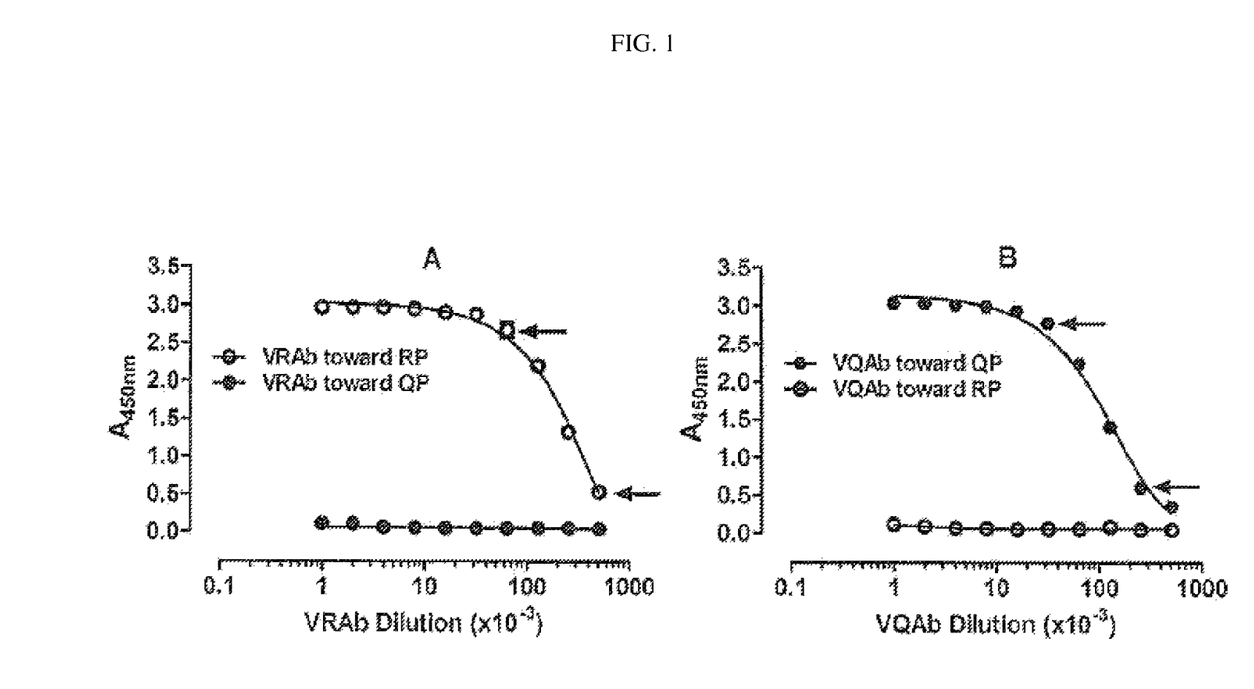
FIG. 1A shows the sensitivity and specificity of the antibody VR against its peptide antigen which contain arginine as the C-terminal residue (RP), as measured by ELISA.
FIG. 1B shows the sensitivity and specificity of the antibody VQ against its peptide antigen which contain glutamine as the C-terminal residue (RP), as measured by ELISA.

Assay for Performance of VR and VQ Antibodies 2-1: Sensitivity and Selectivity of VR and VQ Antibodies VR and VQ antibodies were assayed for sensitivity and selectivity for a peptide antigen having arginine as the C-terminal residue (RP) and a peptide antigen having glutamine as the C-terminal residue after the removal of the arginine residue (QP), respectively, by ELISA (performed at 25° C. for 10 min). The results are shown in FIG. 1. The RP peptide had the amino acid sequence of CKLPECEAVCGKPKNPANPVQR (SEQ ID NO: 1) while the QP peptide had the same amino acid sequence with the exception that the C-terminal R residue was removed, CKLPECEAVCGKPKNPANPVQ (SEQ ID NO: 2).

As shown in FIG. 1, the VR antibody was found to recognize the RP antigen only while the VQ antibody reacted only with the QP antigen. Both the two antibodies VR and VQ had a titer of 512,000 (dilution), with the sensitivity of the VR antibody being twice as high as that of the VQ antibody.

2-2. Comparison with Polyclonal and Monoclonal Antibodies

A. ELISA Assay

VR, VQ, polyclonal (Pα) and monoclonal (MHα and MHβ) antibodies against haptoglobin were examined for reactivity to RP and QP peptides. For this, the antibodies were reacted with various concentrations of each of the antigens, followed by performing an ELISA assay (at 25° C. for 20 min). The results are shown in FIG. 2.

Figure 2:
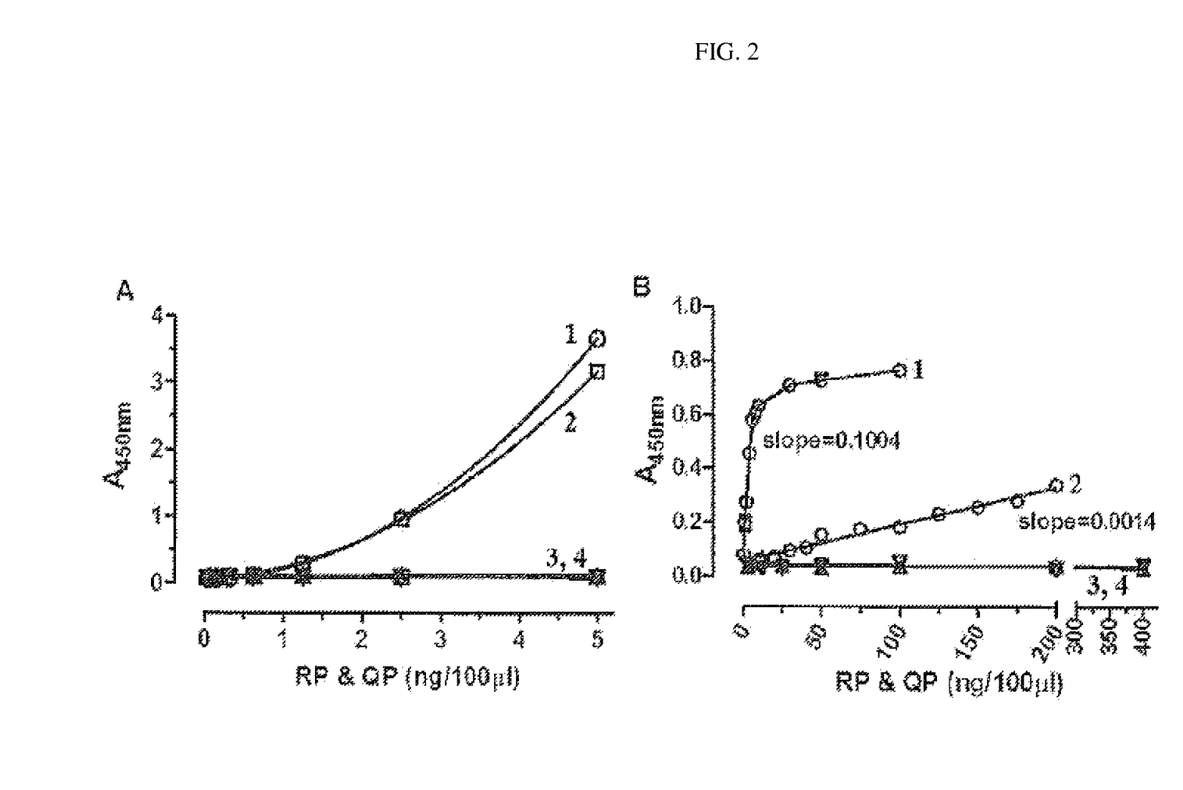
FIG. 2A shows the reactivity of VR and VQ, antibodies against various concentrations of RP and QP peptides, as measured by ELISA.
FIG. 2B shows the reactivity of monoclonal (MHα and MHβ) and polyclonal (Pα) antibodies against various concentrations of RP and QP peptides, as measured by ELISA.

As can be seen in FIG. 2, the antibodies VR and VQ recognized their respective antigen peptides (FIG. 2A) whereas none of the two monoclonal antibodies (MHα and MHβ) reacted with RP and QP peptides (3 and 4 of FIG. 2B) (data for MHβ are not shown due to similarity to MHα). The polyclonal antibody (Pα) was observed to selectively recognize QP, but exhibit very slight reactivity with RP (1 and 2 of FIG. 2B).

The data indicates that the Pα antibody is directed mainly to QP, with very slight reactivity to RP. That is, Pα could recognize the C-terminal site of the haptoglobin chain, but mostly target the C-terminal site devoid of the arginine residue. Incapable of reacting with either of RP and QP, MHα was observed to not recognize the C-terminal site of the haptoglobin alpha chain.

B. 2D-Western Blotting Analysis

The VR antibody, the VQ antibody, and the commercially available monoclonal (MHα and MHβ) and polyclonal (Pα) (Ab Frontier) were assayed for reactivity to the antibodies RP and QP. In this regard, two-dimensional electrophoresis was performed to separate proteins on an IPG (immobilized pH gradient) strip (Bio-Rad 7 cm, pH 4-7) by isoelectric focusing and then on 12% gel by SDS-PAGE, followed by Western blotting. The results are shown in FIG. 3.

Figure 3:
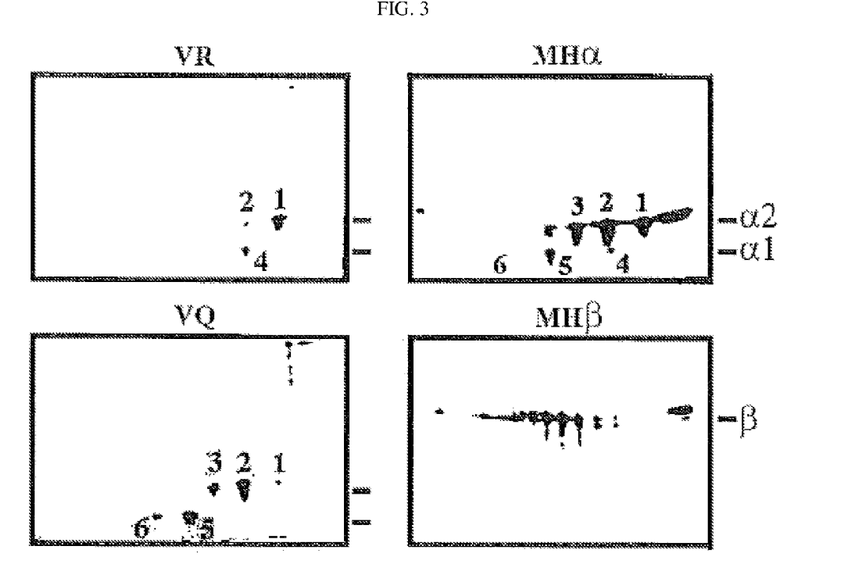
FIG. 3 shows the reactivity of VR antibody, VQ antibody, and monoclonal (MHα and MHβ) antibodies against RP and QP peptides, as measured by Western blotting.

As can be seen in FIG. 3, the VR antibody selectively recognized only Hpα2R (spot 1) among the three position variants of Hpα2 while the VQ antibody showed selectivity for the other two variants of Hpα2 (spots 2 and 3). Also, selective reactivity to haptoglobin alpha 1 (spots 4 to 6) was found in the VR antibody for one position variant (spot 4) and in the VQ antibody for two position variants (spots 5 and 6). This data suggests that only spot 4 of alpha 1 position variants contains the C-terminal arginine residue.

Like MHα, the Pα antibody recognized all the position variants of haptoglobin alpha chain (spots 1 to 6), probably due to the property of polyclonal antibody.

Meanwhile, MHα and MHβ, were observed to recognize only the alpha chain and the beta chain of haptoglobin, respectively.

Taken together, the data obtained above indicates that the VR antibody and the VQ antibody are capable of selectively recognizing the C-terminal arginine site of HpαR and the C-terminal glutamine site of HpαQ, respectively.

Example 3

Performance of HpαR as Lung Cancer-Specific Marker 3-1. ELISA Assay

Serum HpαR levels were examined in 40 sera obtained from a normal male group (normal control, white Caucasian, age: 44.64±2.09) and 60 sera obtained from a male lung cancer patient group (white Caucasian, stage I: 20, stage II: 20, stage III: 14, stage IV: 6), using ELISA. The results are shown in FIG. 4.

Figure 4:
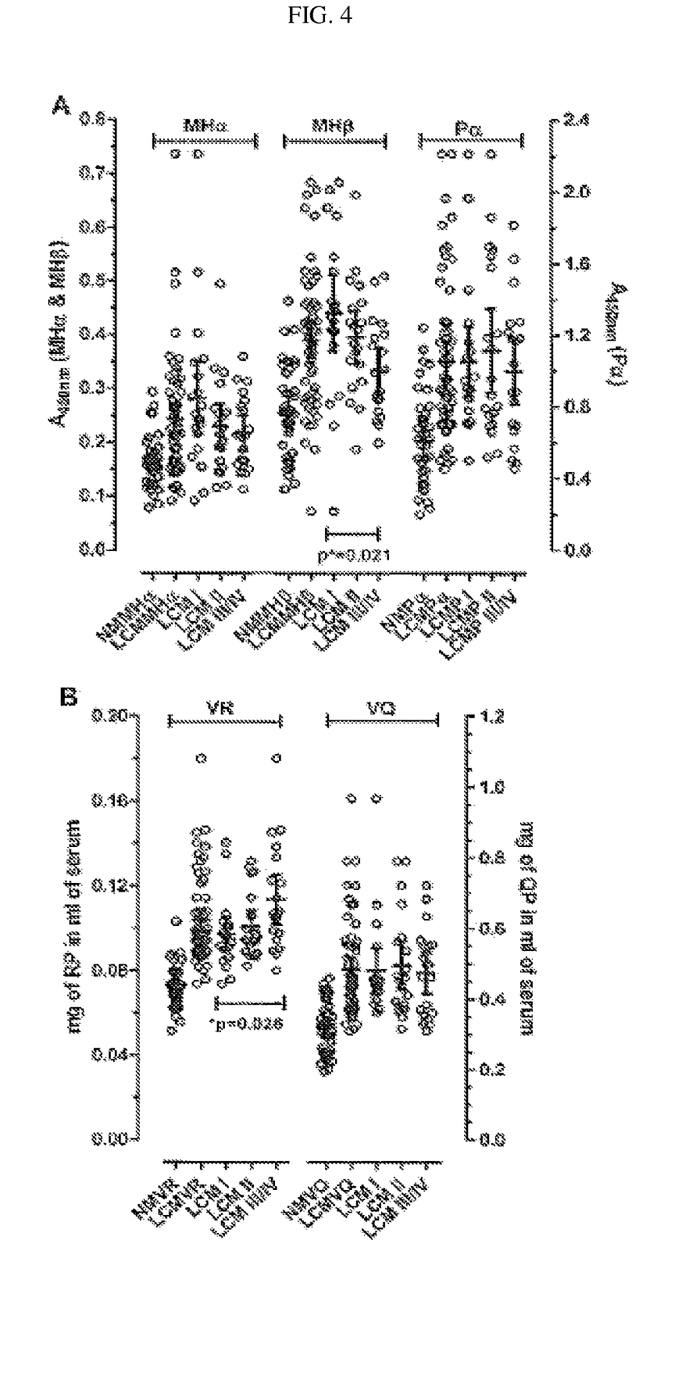
FIG. 4A shows serum HpαR levels in male normal control and male lung cancer patient groups, as measured by ELISA using MHα and MHβ and Pα antibodies.
FIG. 4B shows serum HpαR levels in male normal control and male lung cancer patient groups, as measured by ELISA using VR and VQ antibodies.

As can be seen in FIG. 4, the mean serum HpαR level, as measured with the VR antibody, was found to be 0.07195±0.001596 mg/mL in the normal group and 0.1039±0.002634 mg/mL in the lung cancer patient group, showing that lung cancer increases a serum HpαR level by about 44.4% on average. In the lung cancer patient group, the mean serum HpαR level was measured to be 0.009724±0.003673 mg/mL for stage I, 0.1008±0.003543 mg/mL for stage II and 0.1136±0.005548 mg/mL for stage III/IV, with an increase by 11.7% with the progress from stage I to stage III/IV. The difference in serum HpαR levels according to the progress of lung cancer was evaluated to be significant as analyzed by ANOVA test ($p=0.026$).

The mean serum HpαQ level, as measured with the VQ antibody, was found to be 0.3178±0.01212 mg/mL in the normal group and 0.4833±0.01728 mg/mL in the lung cancer patient group, showing that lung cancer increases the serum HpαQ level by about 52% on average. In the lung cancer patient group, the mean serum HpαQ level was measured to be 0.4799±0.03066 mg/mL for stage I, 0.49061±0.03256 mg/mL for stage II and 0.4738±0.02771 mg/mL for stage III/IV. The serum HpαQ level was increased by about 3.4% with the progress from stage I to stage II, but reduced by about 4.5% with the progress from stage II to stage III/IV.

Since MHα and MHβ, can respectively detect only the alpha chain and the beta chain of haptoglobin (see FIG. 3), the measurements obtained with the two monoclonal antibodies are considered as reflecting the quantities of the alpha and the beta chain of haptoglobin, respectively. In this case, the alpha and the beta chain of haptoglobin were found to decrease in serum level with the progress of lung cancer into higher stages, in contrast to the case of the VR antibody.

Referring to Pα data, the serum level was increased in the early stages (stage I/II), but decreased in the later stages (stage III/IV), like the data of the VQ antibody, which was coincident with the similar results about the reactivities of VQ and Pα to Qp.

Meanwhile, serum Hpα and Hpβ, levels in the lung cancer patient group increased by about 50% and 51.2%, respectively, compared to the normal control. However, Hpα and Hpβ, levels were decreased by about 23.3% and 32.4%, respectively, with the progress of lung cancer from an early to a later phase (stage I to stage III/IV).

Because only the serum HpαR level increases with an increase in the stage of lung cancer, as described above, HpαR can be used as a marker to track the progress of lung cancer.

3-2. ROC Curve Analysis

Measurements of the ELISA performed on sera of the normal control and the patient group using various antibodies (VR, VQ, Pα, MHα and MHβ) were subjected to ROC curve analysis to afford AUC, sensitivity and specificity values for each antibody, and the results are summarized in Table 2, below.

TABLE 2

|  | AUC ± SE | 95% CI | Sensitivity (%) | Specificity (%) | Cut-off value |
|---|---|---|---|---|---|
| VRAb | 0.961 ± 0.0190 | 0.902 to 0.989 | 88.3 | 92.5 | >0.0866 (a) |
| VQAb | 0.885 ± 0.0321 | 0.806 to 0.940 | 93.3 | 65.0 | >0.3448 (a) |
| PαAb | 0.820 ± 0.0420 | 0.730 to 0.889 | 85.0 | 65.0 | >0.6884 (b) |
| MHαAb | 0.765 ± 0.0476 | 0.670 to 0.844 | 70.0 | 81.0 | >0.1876 (b) |
| MHβAb | 0.812 ± 0.0426 | 0.722 to 0.883 | 61.7 | 92.5 | >0.3577 (b) |

As shown in Table 2, when the serum Hpαπlevel was determined using the VR antibody, the AUC (area under curve) value was measured at 0.961±0.0190 mg/mL, the cut-off value at 0.0866 mg/mL, the sensitivity at 88.3% and the specificity at 92.5%, which were superior to other measurements obtained using the other antibodies.

This data indicates that HpαR is more efficient as a lung cancer marker than HpαQ, Hpα (human haptoglobin a chain polyclonal antibody), MHα and MHβ (human haptoglobin α and β chain monoclonal antibodies).

Example 4

Performance of HpαR as Pneumonia Marker 4-1. ELISA Assay

To examine whether the HpαR level in serum is correlated with the inflammation caused by the transient increase of Hp, the HpαR and HpEQ levels in sera of pneumonia patients (male, white Caucasian, n=40), were analyzed by ELISA. Also, serum Hpα and Hpβ levels in pneumonia patients were measured using Pα, MHα and MHβ, which are specific for the alpha and the beta chain of Hp. The results are given in FIG. 5.

Figure 5:
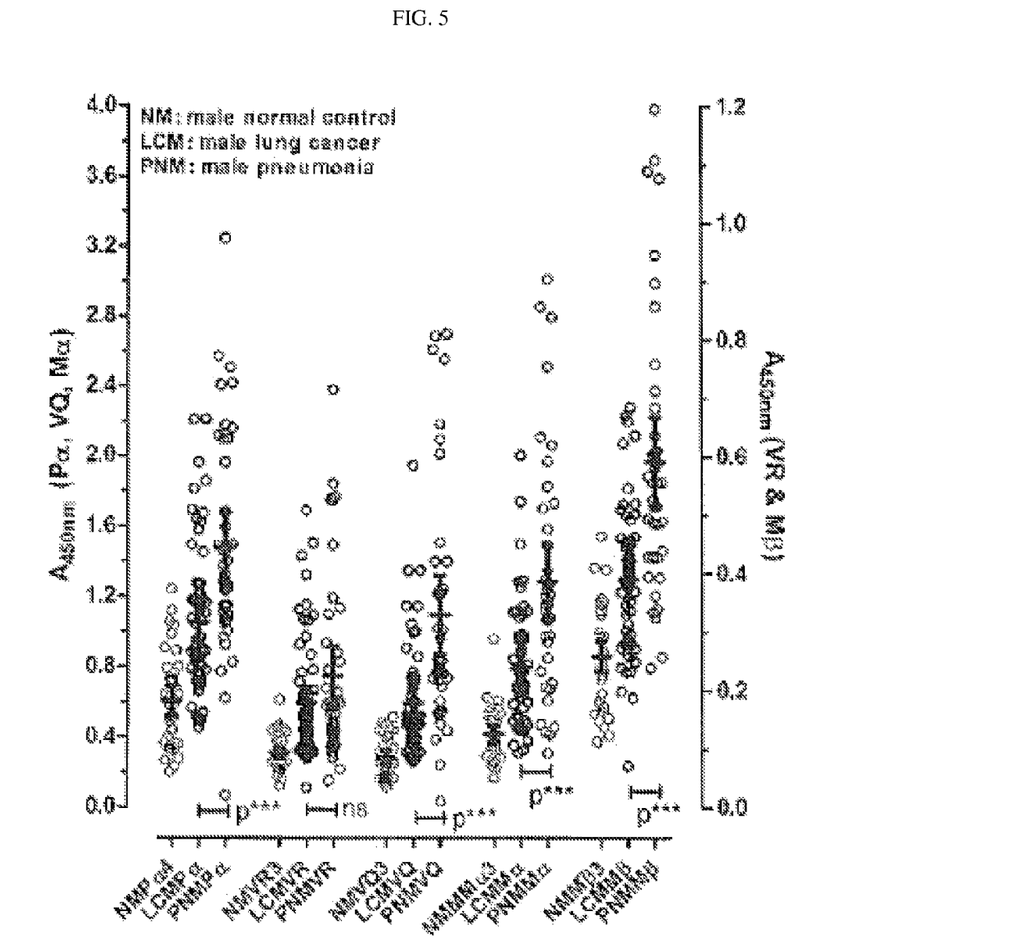
FIG. 5 shows serum HpαR, HpαQ, Hpα and Hpβ levels in pneumonia patients, as measured by ELISA.

As can be seen in FIG. 5, there is no statistical significance in the difference between the pneumonia patient group and the lung cancer patient group solely in the case of the measurements of HpαR obtained with the VR antibody. In all other cases except for HpαR, the serum levels of proteins of interest in the pneumonia patient group were two or more times higher than those in the lung cancer patient group, with clear statistical significance therebetween ($p<0.0001$) (increase fold: 2.45 for Pα, 3.9 for VQ, 3.06 for MHα, 2.3 for MHβ, and 1.38 for VR).

4-2. ROC Curve Analysis

Measurements of the ELISA performed on the sera of the normal control and the patient group using various antibodies (VR, VQ, Pα, MHα and MHβ) were subjected to ROC curve analysis to afford AUC, sensitivity and specificity values for each antibody, and the results are summarized in Table 3, below.

TABLE 3

|       | AUC ± SE        | 95% CI          | Sensitivity (%) | Specificity (%) | Cut-off value (A450 nm) |
|-------|-----------------|-----------------|-----------------|-----------------|-------------------------|
| VRAb  | 0.782 ± 0.0454  | 0.688 to 0.858  | 71.7            | 72.5            | >0.1019                 |
| VQAb  | 0.924 ± 0.0259  | 0.854 to 0.968  | 78.3            | 95.0            | >0.4621                 |
| PαAb  | 0.886 ± 0.0420  | 0.807 to 0.941  | 83.3            | 82.5            | >0.802                  |
| MHαAb | 0.910 ± 0.0476  | 0.837 to 0.958  | 78.3            | 95.0            | >0.2547                 |
| MHβAb | 0.870 ± 0.0426  | 0.788 to 0.929  | 71.7            | 92.5            | >0.3577                 |

Comparing the data of Table 2 to the data of Table 3 shows that lower analysis values of AUC, sensitivity and specificity were obtained in the pneumonia patient group than in the lung cancer patient group only when HpαR was analyzed using the VR antibody. This result indicates that the increase in serum HpαR level with the progress of lung cancer does not come from the inflammation condition of pneumonia. The increase in the serum level of HpαR, which is the C-terminal arginine-containing variant of the haptoglobin alpha chain, occurs during the onset of lung cancer as measured by the VR antibody rather than the simple increase of serum haptoglobin as in typical inflammation. Accordingly, the increased serum HpαR level in lung cancer patients is considered to be attributed not only to the increase of serum Hp level itself, but also mainly to the increased proportion of HpαR amongst all Hp proteins in association with the onset and progress of lung cancer.

Example 5

Complementarity of HpαR and HpαQ Variant as Lung Cancer Marker

Antibody mixtures having various ratios of the VR and VQ antibodies, with the total concentration of the two antibodies maintained at 1/128,000 (unsaturated condition of each antibody), were applied to sera of the normal control group and the lung cancer patient group to quantitatively analyze the respective antigen proteins concurrently. The measurements were subjected to ROC curve analysis to afford AUC values indicative of the probability of determining cancer. The results are shown in FIG. 6.

Figure 6:
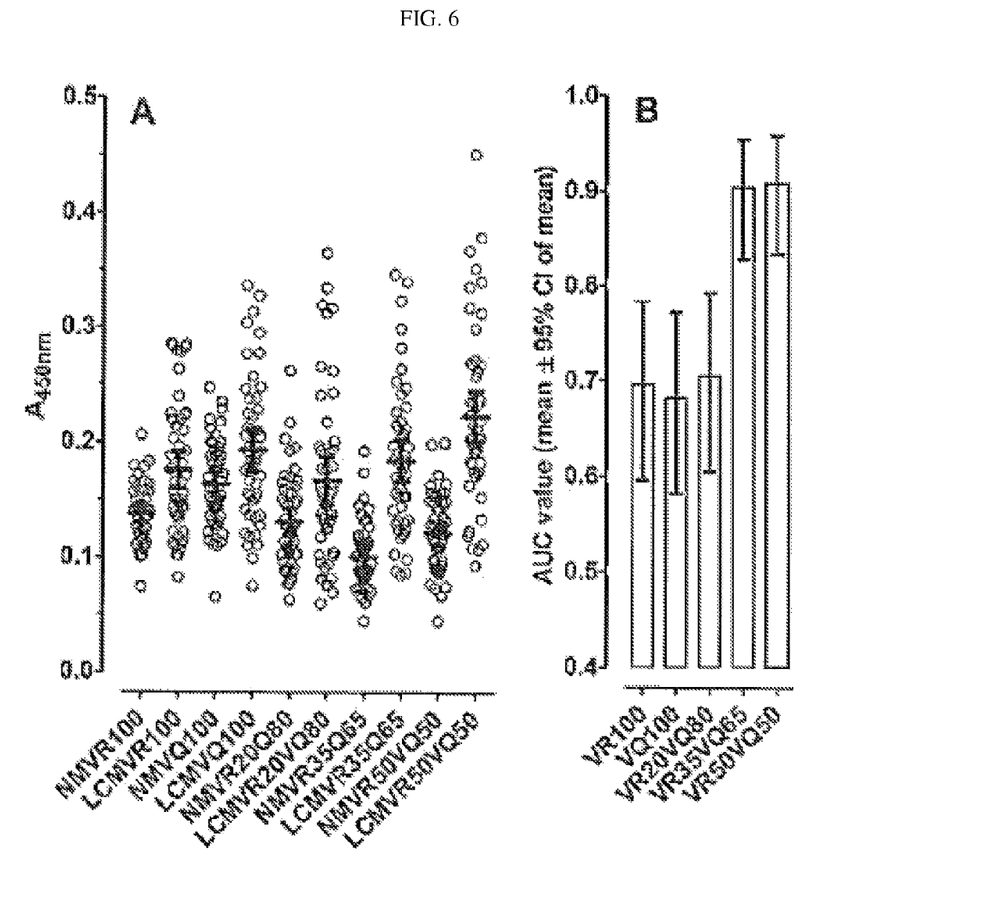
FIG. 6A shows serum levels of the antigens corresponding to VR and VQ in normal control and lung cancer patient groups, as measured by ELISA using a mixture of VR antibody and VQ antibody.
FIG. 6B shows an ROC curve analysis results of the measurements depicted by FIG. 6A.

As can be seen in FIG. 6, AUC values were increased by about 30% when an antibody mixture containing equal amounts of the two antibodies (VR50VQ50) was used compared to when the antibodies were used individually (VR100 and VQ100), suggesting that the concurrent use of both antibodies sharply increases the ability to discriminate lung cancer and that HpαR and HpαQ function as independent markers for lung cancer. Taken together, the above data indicates that the increased level of HpαR with the progress of lung cancer and the increased level of HpαQ with the synthesis of haptoglobin upon the onset of lung cancer have a synergistic contribution on the increased ability to discriminate lung cancer.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

Exhibiting high concentrations in the sera of lung cancer patients, as described hitherto, HpαR can be used to diagnose and prognosticate lung cancer in an early stage and thus is useful as a diagnostic marker for lung cancer.

---

The invention claimed is:

1. A method for diagnosing lung cancer, comprising:
   (a) obtaining a blood sample from a subject and isolating a serum fraction from the blood sample;
   (b) contacting the serum fraction with an anti-HpαR (haptoglobin alpha 2 chain with C-terminal arginine) antibody;
   (c) measuring the concentration of HpαR in the serum fraction; and
   (d) diagnosing the subject with lung cancer based on the concentration of the HpαR;
   wherein the anti-HpαR antibody specifically binds to a C-terminal amino acid sequence CKLPECEAVCGKPKNPANPVQR (SEQ ID NO: 1) of HpαR and not to a C-terminal sequence of CKLPECEAVCGKPKNPANPVQ (SEQ ID NO: 2) of HpαQ (haptoglobin alpha 2 chain without C-terminal arginine).

2. The method of claim 1, wherein the concentration of HpαR is between 0.009724±0.003673 mg/mL and 0.1136±0.005548 mg/mL.

3. The method of claim 1, wherein a diagnosis of stage I lung cancer is made if the HpαR concentration is 0.009724±0.003673 mg/mL.

4. The method of claim 1, wherein a diagnosis of stage II lung cancer is made if the HpαR concentration is 0.1008±0.003543 mg/mL.

5. The method of claim 1, wherein a diagnosis of stage III or IV lung cancer is made if the HpαR concentration is 0.1136±0.005548 mg/mL.

6. The method of claim 1, wherein the measuring step is performed using an ELISA test.

7. The method of claim 1, wherein the measuring step is performed using an assay selected from the group consisting of radioimmunoassay (RIA), sandwich assay, Western blotting, immunoprecipitation, fluorescent immunoassay, enzyme-substrate coloring assay and antigen-antibody aggregation.

* * * * *

SEQUENCE LISTING

<160> NUMBER OF SEQ ID NOS: 2

<210> SEQ ID NO 1
<211> LENGTH: 22
<212> TYPE: PRT
<213> ORGANISM: Artificial Sequence
<220> FEATURE:
<223> OTHER INFORMATION: HP-alphaR

<400> SEQUENCE: 1

Cys Lys Leu Pro Glu Cys Glu Ala Val Cys Gly Lys Pro Lys Asn Pro
1               5                   10                  15

Ala Asn Pro Val Gln Arg
            20

<210> SEQ ID NO 2
<211> LENGTH: 21
<212> TYPE: PRT
<213> ORGANISM: Artificial Sequence
<220> FEATURE:
<223> OTHER INFORMATION: HP-alphaQ

```
<400> SEQUENCE: 2

Cys Lys Leu Pro Glu Cys Glu Ala Val Cys Gly Lys Pro Lys Asn Pro
1               5                   10                  15

Ala Asn Pro Val Gln
            20
```